United States Patent [19]
Nies

[11] Patent Number: 6,110,205
[45] Date of Patent: Aug. 29, 2000

[54] IMPLANT MATERIAL HAVING AN EXCIPIENT/ACTIVE COMPOUND COMBINATION

[75] Inventor: Berthold Nies, Fränkisch-Crumbach, Germany

[73] Assignee: Merck Patent Gesellschaft mit Beschrankter Haftung, Germany

[21] Appl. No.: 09/102,013

[22] Filed: Jun. 22, 1998

[30] Foreign Application Priority Data

Jun. 21, 1997 [DE] Germany ................ 197 26 412

[51] Int. Cl.⁷ ................ A61F 2/02; A61F 2/28
[52] U.S. Cl. ................ 623/11.11; 623/16.11; 623/23.72; 623/23.76; 623/923; 606/151; 424/423; 427/2.26; 427/2.29; 427/2.31
[58] Field of Search ............... 623/11–16, 66.1, 623/11.11, 16.11, 17.11, 20.17, 23.29, 23.3, 23.36, 23.57, 23.72–23.76, 923; 606/151, 154, 228; 424/422, 423–426; 427/2.1, 2.14, 2.16, 2.24, 2.26, 2.29, 2.31, 606, 424

[56] References Cited

U.S. PATENT DOCUMENTS

| 5,222,978 | 6/1993 | Kaplan et al. | 606/228 |
|---|---|---|---|
| 5,278,201 | 1/1994 | Dunn et al. | 523/113 |
| 5,399,353 | 3/1995 | Bartnik et al. | |
| 5,597,897 | 1/1997 | Ron et al. | 530/350 |
| 5,679,723 | 10/1997 | Cooper et al. | 523/115 |
| 5,717,030 | 2/1998 | Dunn et al. | 523/111 |
| 5,776,193 | 7/1998 | Kwan et al. | 623/11 |
| 5,968,543 | 10/1999 | Heller et al. | 424/425 |

FOREIGN PATENT DOCUMENTS

| 0 258 780 A2 | 3/1988 | European Pat. Off. . |
|---|---|---|
| 0 520 237 | 6/1992 | European Pat. Off. . |
| 97/25366 | 7/1997 | WIPO . |

*Primary Examiner*—David H. Willse
*Assistant Examiner*—Tram A. Nguyen
*Attorney, Agent, or Firm*—Millen, White, Zelano & Branigan, P.C.

[57] ABSTRACT

The present invention relates to porous implant materials which are loaded with an excipient/active compound combination, the excipient components used being oligomeric esters of polyhydric alcohols and α-hydroxy acids.

14 Claims, No Drawings

IMPLANT MATERIAL HAVING AN EXCIPIENT/ACTIVE COMPOUND COMBINATION

The invention relates to porous implant materials which are charged with an excipient/active compound combination, where, as the excipient component, oligomeric esters of polyhydric alcohols and α-hydroxy acids are used.

BACKGROUND OF THE INVENTION

Porous implant materials are understood, for example, as meaning bone substitute materials which are used as implants for the substitution or the reconstitution of bone structures on account of defects after illness- or accident-related surgical interventions. Examples which may be mentioned are molded implant articles such as bone prostheses of many different types, bone connecting elements, for example in the form of intramedullary nails, bone screws and osteosynthesis plates, implant materials for filling spongiosa bone defects or tooth extraction cavities as well for the plastic surgery treatment of contour defects in the jaw/face area.

This term furthermore includes surface-structured implants, such as, for example, dental implants or metal prostheses for the replacement of joints. Furthermore, these are also to be understood as meaning non-woven materials, membranes, fabric, laminates and the like for wound coverings, skin replacement, vascular prostheses or alternatively ligament replacement.

For the healing process, those implant materials which have a high bioactivity are to be regarded as particularly favorable, in that they are taken up in the body and then integrated into it. In the case of bone substitute material, this means that it should soon coalesce firmly and permanently with endogenous tissue, in particular with the bone. DE 41 21 043 describes a bone substitute material which contains, in a porous matrix, one or more polypeptides having the biological action of fibroblast growth factors. Good results are indeed obtained there in the stimulation of bone growth into the porous structure of the implant, but there are also some still unsolved problems. On the one hand, the stability of the peptide growth factors applied in dissolved form can cause problems and on the other hand the biological action cannot be optionally and reproducibly set due to the uncontrolled release. These problems of stability and uncontrolled release are also to be found in the case of other active compounds, such &s, for example, antibiotics, cytostatics or other growth-promoting substances with which the implant material is charged.

SUMMARY

It was therefore desirable to find a combination comprising the active compound(s) which can be applied easily to the porous implant material and which also protects sensitive active compounds so that their activity is retained, and where the release from the porous implant takes place in a manner which affords reproducibility of the biological/pharmacological action.

It has now been found that a system comprising an excipient component, which essentially consists of an oligomeric ester of polyhydric alcohols and α-hydroxy acids, and one or more active compound components is outstandingly able to overcome these problems.

The invention therefore relates to a porous implant material which is charged with an excipient/active compound combination, the excipients used being oligomeric esters of polyhydric alcohols and α-hydroxy acids.

The invention also relates to a process for the preparation of an implant material which is charged with an excipient/active compound combination, which is characterized in that the oligomeric esters are dissolved in an organic solvent and the active compound(s) is/are introduced therein, and in that this mixture is then applied to the porous implant material, the solvent is removed and, if appropriate, the implant material is finally packed in sterile form.

Upon further study of the specification and appended claims, further objects and advantages of this invention will become apparent to those skilled in the art.

As the so-called excipient component, oligomeric esters of polyhydric alcohols and α-hydroxy acids (in the following also called AHA in short) are thus used. Polymers or oligomers of this type are known in principle. For example, it is known that high-polymeric esters of selected lower hydroxy acids, to be specific in particular lactic acid, have high body compatibility and are employed in operative technique, for example, as body-compatible and body-absorbable thread material, which is degraded in the course of weeks or months and flushed out of the body.

Oligomeric esters, in particular of lactic acid and/or glycolic acid, which have an average degree of oligomerization of up to 100, are disclosed in DE 36 20 685. The use of these esters as absorbable excipients and/or film-forming agents in compositions for covering human or animal skin is described there.

The oligomers used in the invention are distinguished by an average degree of oligomerization of the selected acid of up to approximately 30 and preferably up to approximately 10.

The preparation of such oligomers from hydroxycarboxylic acids is known and can in principle be carried out directly by polycondensation of the hydroxycarboxylic acids or hydroxycarboxylic acid mixtures, but it is useful for the specific setting of the degree of oligomerization to add, in a known manner, coreactants for the regulation of the degree of oligomerization, where mono- or polyhydric alcohols or organic acids may primarily be suitable here. The two ester-forming groups of the monomers or of the oligomers, i.e. the hydroxyl group on the one hand and the carboxyl group on the other hand, in fact generally suggest themselves as reactive sites.

In particular, in preferred embodiments alcohols having up to 4, in particular having up to 3, hydroxyl groups are suitable. In the last-mentioned case, the alcohol is in particular glycerol, which leads to extremely varied products by reaction with the AHA oligomers. Examples of further, particularly preferred alcohols are: ethylene glycol, 1,2- or 1,3-propylene glycol, butylene glycol, trimethylolpropane, low molecular weight polyethylene glycols, polypropylene glycol, 1,5-pentanediol or alternatively polyhydric alcohols, sugars or sugar alcohols.

In the field of the co-use of carboxylic acids, on the one hand physiologically tolerable carboxylic acids, in this case in particular monocarboxylic acids, may be of interest, but also polyfunctional carboxylic acids, for example di- or tricarboxylic acids.

The oligomeric hydroxycarboxylic acids or their derivatives are prepared in a manner known per se. Of course, in all cases—i.e. both in the case of the α-hydroxycarboxylic acids and in the case of the co-reactants—not only the free reactive components of the type mentioned in each case, but also those derivatives may be employed which form the desired polyester oligomers in a manner known per se under the conditions of the esterification or transesterification. The esters of the hydroxy acids, for example, are thus suitable, furthermore also the easily handleable dimerization products, for example, of lactic acid and/or glycolic acid, i.e. the lactide and/or the glycolide, will be employed.

The polycondensation reaction is in this case customarily carried out by heating the starting materials to a temperature above the melting point, preferably in the presence of a catalyst, in particular of an esterification catalyst, under anhydrous conditions in an inert gas atmosphere. The amount and type of the catalyst used determine the process temperature and the duration of the reaction. Since the conversion of the reactions is normally nearly 100%, the composition of the final products can be easily controlled by the addition of the reaction participants. Polycondensation reactions of this type are well known to the person skilled in the art. A detailed listing of all types of reaction conditions is therefore not necessary here.

The α-hydroxy acids used are preferably the compounds listed in the following: glycolic acid and lactic acid, which both occur in the metabolism of the living organism and are processed or excreted by the body, lactic acid being used here in the form of its racemate or alternatively in the form of its optical antipodes or as any desired mixtures of the optical antipodes; α-hydroxybutyric acid, α-hydroxyvaleric acid, trimethylene carbonate, ε-caprolactone or alternatively dioxanone.

Very particularly preferably, glycolic acid and/or lactic acid or their dimerization products or alternatively trimethylene carbonate or caprolactone are employed here.

According to the invention, it is possible to use either homooligomeric or heterooligomeric esters. In the case of so-called homooligomeric esters, this means that only a single α-hydroxy acid or one of its reactive derivatives, e.g. lactic acid alone, is used for the preparation of the oligomeric esters, or in the case of the heterooligomers this means that mixtures of different α-hydroxy acids are employed in the polycondensation reaction for the preparation of the oligomeric products. Preferably, glycolic acid, trimethylene carbonate or alternatively caprolactone also occurs as a quantitatively distinctly smaller part in cooligomers with lactic acid or other α-hydroxy acids.

Particularly preferred oligomers are synthesized, for example, from the following monomers: glycerol, lactide and glycolide; ethylene glycol, lactic acid and glycolic acid; propylene glycol, lactide and glycolide;

glycerol and lactide; glycerol, glycolic acid and α-hydroxybutyric acid; ethylene glycol and α-hydroxyvaleric acid; glycerol and ethyl lactate;

glycerol, trimethylene carbonate and glycolic acid;

ethylene glycol and lactide; ethylene glycol, glycolic acid and ethyl lactate; glycerol, glycolic acid and ε-caprolactone.

The listing of the preceding compounds is only a small selection of particularly preferred products, it should in no case have limiting character.

Suitable active compounds can be all pharmaceutical active compounds which are useful from their profile of action in bone cements, in bone substitute materials, implantation materials and in implantable pharmaceutical depots. Suitable active compounds are thus preferably cytostatics such as methotrexate, cisplatin, cyclophosphamide, fluorouracil, doxorubicin etc., antibiotics such as gentamycin, clindamycin, vancomycin, teicoplanin etc., and furthermore antiseptics and growth-promoting substances.

Growth-promoting substances which should be mentioned here are, for example, the fibroblast growth factors (FGF), which belong to the endogenous peptide growth factors class. FGFs are known as active, vessel-forming factors which are responsible, inter alia, for neovascularization in wound healing, and also as bone growth-promoting substances. Closer details of the FGFs including their modification products, of their isolation and preparation, their structure, their biological activities and their mechanisms as well as of appropriate medicinal applications can be taken from the meanwhile extensive specialist literature. A comprehensive survey is offered, for example, by A. Baird and P. Bbhlen, Fibroblast Growth Factors, in: Peptide Growth Factors and their Receptors I (editors: M. B. Sporn and A. B. Roberts) Springer Verlag Berlin, Heidelberg, N.Y. 1990.

The oligomeric esters are largely unreactive under normal reaction conditions provided they are kept free of moisture. For this reason, they are compatible with very many interesting active compounds. Active compounds which are incorporated into these oligomeric esters thus remain stable over a long period of time. In the direct application of, for example, proteins to implant surfaces (e.g., ENDOBON™, a hydroxyapatite ceramic suitable as a bone graft substitute), the previously freeze-dried protein is reconstituted in aqueous solution. Even in this dissolved state, a slow inactivation frequently occurs. During the application to the implant, the protein comes into contact with the excipient surface and can be denatured on or irreversibly bound to the surface. Moreover, as in the case of ENDOBON™, the implant can release soluble components which, for example, severely change the pH of the loading solution and thereby contribute to the inactivation of active compound.

In the case according to the invention, the active compound is not dissolved, but preferably suspended in the oligomeric ester as a micronized lyophilizate and applied to the excipient surface as a more or less thick layer. The active compound is thus neither dissolved, neither does it come into contact in dissolved form with the excipient. Only after implantation or other introduction into the body does the active compound come into contact with an aqueous solution, and release then takes place both by slow dissolution of the hydrolysable oligomeric ester and by diffusion of water into the ester matrix, dissolution of the active compound in the matrix and subsequent diffusion of the dissolved active compound through the matrix. This process is adjustable within wide limits by the coordinated selection of oligomeric ester, active compound preparation, layer thickness and, if appropriate, additives, via which the release of the active compound can be controlled. Additives of this type are preferably known substances which increase the absorption of water into the oligomeric esters and thereby increase the release of the active compound. Release-promoting effects of this type are known, for example, of amino acids, sugars, certain organic solvents and also readily water-soluble bodily tolerable substances (DE 44 33 201). In particular in comparison to direct loading with active compound solution, a release of the active compound which is controllable and essentially more insensitive to external influences results thereby.

The preparation of the excipient/active compound combination is carried out as follows. The oligomeric esters are dissolved in simple anhydrous, organic solvents. Possible solvents are, for example, acetone, N-methylpyrrolidone, 2-pyrrolidone, ethyl acetate, dioxane or tetrahydrofuran. The active compound(s) is/are suspended or dissolved, preferably as a micronized lyophilizate, in these solutions. This solution or suspension is then applied to the porous implant material. Then the solvent is removed and preferably packed and sterilized, for example by gamma irradiation.

The nature of the loading depends, inter alia, on the implantation material and the active compound. The loading level can be very different and depends very strongly on the specific activity of the active compound.

For the loading level, the following values mentioned by way of example can be indicated as suitable standard values. Preferably the loading with antibiotics is 5% to 80%, in particular preferably 10% to 60% (in each case based on the oligomer). In the case of the growth factors (highly active peptides, proteins), the loading is 0.01 μg/ml to 250 mg/ml, preferably 0.1 μg/ml to 100 mg/ml.

In the case of implants, such as hip or knee endoprostheses, the suspension can be advantageously pressed onto the metal surface directly via a metering apparatus. This can preferably be carried out by means of a program controlled robot. On the other hand, of course, immersion processes and spraying-on techniques are possible.

In the case of porous granules, such as, for example, Endobon granules, the customary techniques of pharmaceutical technology can be used for many matrix-active compound combinations, such as, for example, spraying in a coating pan.

Another possibility also consists in packing the individual components in sterile form and making them available in a ready-to-use set. Thus the loaded implant according to the invention can be prepared directly before use.

The invention thus also relates to an implant material which is characterized in that it is present in the form of a ready-to-use set of two or more separate components, one component of which comprises the porous implant material and another component a solution of the excipient/active compound combination, or optionally alternatively contains the individual components from which the excipient/active compound combination can be prepared.

Such an embodiment is particularly expedient for effectively combating stability problems which could occur on long-term storage of already ready-packed implant materials according to the invention. The use of the implant materials according to the invention is effected by loading the porous implant material with the excipient/active compound combination in the manner described shortly before or during the surgical intervention or the corresponding treatment. In this case, the excipient solution and the active compound(s) can either be already mixed or alternatively packed separately in sterile form. If they are packed separately, these must, of course, first be mixed as described before application to the implant material. The individual components are in this case prepared and packed separately in sterile form and, if required, combined under aseptic conditions to give the ready-to-use implant material.

For the implant materials according to the invention, in principle all known and customary implant materials can be used provided these have a porous matrix or surface, or are a surface-structured material. Implant materials can be divided into the classes of mineral materials in particular ceramic materials, physiological acceptable metallic materials, physiologically acceptable polymer materials and composite materials of two or more materials of the type mentioned. These materials can as a whole form a porous matrix, for example in the form of porous shaped implant articles, or only certain components of the material can be present as a porous material or certain areas of a molded implant article can be a porous matrix. The last two cases can be realized, for example, in the form in which a composite material or a bone cement contains a porous component or an implant is provided with a porous surface coating or an appropriately roughened surface.

Possible mineral materials are, for example, materials which are based on calcium-containing materials, such as, in particular, calcium carbonate, calcium phosphates and systems derived from these compounds. From the calcium phosphate group, hydroxyapatite, tricalcium phosphate and tetracalcium phosphate may be mentioned as preferred.

Implant materials on a mineral basis, however, mostly only guarantee a high mechanical stability if they are employed as ceramics, i.e. in the form of materials or manufactured articles sintered at sufficiently high temperatures.

Details of bone ceramics and particularly favorable processes for their production can be taken, for example, from the patent documents DE 37 27 606, DE 39 03 695, DE 41 00 897 and DE 40 28 683.

The great advantage of the present invention is that the excipient/active compound combination can be applied using all types of materials, largely independently of the material used. The implant materials only have to be formed or shaped such that they contain, as mentioned above, a porous matrix for the uptake of the excipient/active compound combination and re-release in the body, expediently at least principally in the contact area with the body tissue. These conditions are also fulfilled, for example, by implants made of metallic materials which are porous per se or have a porous surface coating, or which have a surface which has a porous structure or is at least roughened. The same applies to implants made of polymeric materials, other ceramic materials or from composite materials.

Examples of such surface-structured implants which may be mentioned are dental implants or alternatively metal prostheses for joint replacement. The metallic material mainly employed is titanium or a titanium alloy.

Other suitable implant materials which may be mentioned here by way of example are materials which are employed for wound coverings, as a skin substitute, vascular prostheses or alternatively ligament replacement, such as nonwoven materials, membranes, fabric or laminates.

In principle, the implant materials according to the invention can be present not only as shaped implant articles, but also in powder or granule form, depending on what the site of use and the intended application requires.

The preceding listing of possible porous implant materials only represents a small selection of particularly preferred products, it should in no case have limiting character.

Using the loading according to the invention of porous implant materials with the excipient/active compound combination described here, it is thus now possible to produce a system which protects and stabilizes the sensitive active compounds and further from which the active compound is released slowly, over a relatively long period of time, in a controlled manner. Reproducibility of the biological/pharmacological action is thus also guaranteed.

Without further details, it is assumed from this that a person skilled in the art can use the above description to the widest extent. Because of this, the preferred embodiments are only to be interpreted as descriptive, and in no way as a disclosure which is limiting in any manner.

The entire disclosure of all applications, patents and publications, cited above and below, and of corresponding German application No. 197 26 412.3, filed Jun. 21, 1997 is hereby incorporated by reference.

EXAMPLES

The following examples are intended to clarify the present invention.

Example 1

100.0 g of glycerooligolactide of the composition 1:26 (parts of glycerol: parts of lactic acid) are dissolved in 250 ml of acetone. 15.3 g of micronized gentamycin sulfate (corresponding to 10 g of activity) are added to this solution and it is intensively mixed. The suspension thus obtained is applied to a hip prosthesis shaft made of titanium alloy such that the loading per $cm^2$ of surface area is 2.5 mg of gentamycin activity. Then the acetone is removed at a temperature of 30° C., and the prosthesis shaft is packed and sterilized in the pack by gamma irradiation. The product is ready-to-use thus.

Example 2

100.0 g of glycerooligolactide (GOL) of the composition 1:26 (parts of glycerol: parts of lactic acid) are dissolved in 150 ml of N-methylpyrrolidone. 200 µg of a powdered lyophilizate of basic fibroblast growth factor (bFGF) which, if desired, can additionally contain various auxiliaries, are added to 5 ml of this solution. The mixture is uniformly stirred and then mixed with 25 ml of porous granules of bone ceramic (particle size about 3–6 mm). The product thus obtained is additionally mixed 1:1 with comminuted spongiosa before implantation and can then be implanted in a bone defect.

As a ready-to-use set, this consists of the following components:
5 ml of solution of GOL in NMP, about 40% strength
200 µg of bFGF lyophilizate (plus auxiliaries, e.g. sucrose)
25 ml of bone ceramic granules
Vessels and appliances for storing and mixing
All components in sterilized form.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A porous implant material which comprises, loaded in the porous implant material, a combination of an excipient and an active compound, the excipient comprising an oligomeric ester of a polyhydric alcohol and an α-hydroxy acid and the active compound being suspended, not dissolved, in the oligomeric ester as a micronized lyophilizate.

2. The porous implant material according to claim 1, wherein the α-hydroxy acid is lactic acid, glycolic acid, caprolactone, trimethylene carbonate or α-hydroxybutyric acid.

3. The porous implant material according to claim 1, wherein the ester is from a mixture of α-hydroxy acids.

4. The porous implant material according to claim 1, wherein the polyhydric alcohol is glycerol, ethylene glycol, propylene glycol or a polyethylene glycol.

5. The porous implant material according to claim 1, wherein the porous implant material is a porous bone substitute material, surface-structured implant, non-woven material, membrane, fabric or laminate.

6. The porous implant material according to claim 1, wherein the active compound is a cytostatic, an antibiotic, an antiseptic, a bone growth-promoting substance, a substance which affects growth of tissue into the porous structure of the implant material or a combination thereof.

7. The porous implant material of claim 1, wherein the oligomeric ester has an average degree of oligomerization of the α-hydroxy acid of up to 30.

8. The porous implant material of claim 1, wherein the oligomeric ester has an average degree of oligomerization of the α-hydroxy acid of up to 10.

9. The porous implant material of claim 1, wherein the implant material contains the combination of the excipient and active compound loaded in the implant material by impregnation or as a coating on a porous surface of the implant material.

10. A process for the preparation of a porous implant material, which comprises, loaded in the porous implant material, a combination of an excipient and active compound, the excipient comprising an oligomeric ester of a polyhydric alcohol and an α-hydroxy acid, said process comprising dissolving the oligomeric ester in an organic solvent, introducing the active compound therein, applying this mixture to the porous implant material, and removing the solvent.

11. The process of claim 10, further comprising packaging the porous implant material in sterile form.

12. A porous implant material which comprises, loaded in the porous implant material, a combination of an excipient and an active compound, the excipient comprising an oligomeric ester of a polyhydric alcohol and an α-hydroxy acid, the implant material being present in the form of a ready-to-use implant material of two or more separate components, one component of which comprises the porous implant material and another component of which comprises a solution of the excipient and active compound combination or components from which the excipient and active compound combination is prepared.

13. The porous implant material according to claim 12, wherein the two or more separate components are prepared separately and packed in sterile form to give the ready-to-use porous implant material.

14. The porous implant material of claim 13, wherein the two or more separate components are combined under aseptic conditions to give the ready-to-use porous implant material.

* * * * *

UNITED STATES PATENT AND TRADEMARK OFFICE
Certificate

Patent No. 6,110,205                                                                Patented: August 29, 2000

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Berthold Nies, Fränkisch-Crumbach, Germany; and Wolfgang Ritter, Offstein, Germany.

Signed and Sealed this Second Day of April 2002.

CORRINE M. MCDERMOTT
*Supervisory Patent Examiner*
Art Unit 3738